(12) United States Patent  
VanDanacker

(10) Patent No.: US 7,697,994 B2  
(45) Date of Patent: Apr. 13, 2010

(54) REMOTE SCHEDULING FOR MANAGEMENT OF AN IMPLANTABLE MEDICAL DEVICE

(75) Inventor: John P. VanDanacker, Greenfield, MN (US)

(73) Assignee: Medtronic, Inc., Minneapolis, MN (US)

( * ) Notice: Subject to any disclaimer, the term of this patent is extended or adjusted under 35 U.S.C. 154(b) by 1109 days.

(21) Appl. No.: 11/236,704

(22) Filed: Sep. 27, 2005

(65) Prior Publication Data

US 2006/0085040 A1    Apr. 20, 2006

Related U.S. Application Data

(63) Continuation-in-part of application No. 10/871,591, filed on Jun. 18, 2004, now Pat. No. 7,565,197.

(51) Int. Cl.  
*A61N 1/00* (2006.01)

(52) U.S. Cl. ...................................................... 607/60

(58) Field of Classification Search .................. 607/32, 607/60, 30, 31  
See application file for complete search history.

(56) References Cited

U.S. PATENT DOCUMENTS

| | | | |
|---|---|---|---|
| 5,312,453 A | 5/1994 | Shelton et al. | |
| 5,345,362 A | 9/1994 | Winkler et al. | |
| 5,545,186 A | 8/1996 | Olson et al. | |
| 5,987,352 A | 11/1999 | Klein et al. | |
| 6,169,925 B1 | 1/2001 | Villaseca et al. | |
| 6,240,317 B1 | 5/2001 | Villaseca et al. | |
| 6,249,703 B1 | 6/2001 | Stanton et al. | |
| 6,363,282 B1 | 3/2002 | Nichols et al. | |
| 6,418,346 B1 | 7/2002 | Nelson et al. | |
| 6,438,408 B1 | 8/2002 | Mulligan et al. | |
| 6,442,433 B1 | 8/2002 | Linberg | |
| 6,443,891 B1* | 9/2002 | Grevious | 600/302 |
| 6,471,645 B1 | 10/2002 | Warkentin et al. | |
| 6,482,154 B1 | 11/2002 | Haubrich et al. | |
| 6,497,655 B1 | 12/2002 | Linberg et al. | |
| 6,544,173 B2* | 4/2003 | West et al. | 600/300 |
| 6,561,975 B1 | 5/2003 | Pool et al. | |
| 6,564,104 B2 | 5/2003 | Nelson et al. | |
| 6,622,045 B2 | 9/2003 | Snell | |
| 6,647,299 B2 | 11/2003 | Bourget et al. | |
| 2001/0027331 A1* | 10/2001 | Thompson | 607/60 |

(Continued)

OTHER PUBLICATIONS

International Search Report, PCT/US2006/036624, Jan. 25, 2007, 5 Pages.  
U.S. Appl. No. 10/941,318, Osborn et al.  
U.S. Appl. No. 10/072,782, Webb et al.  
U.S. Appl. No. 09/441,405, Bardy.  
U.S. Appl. No. 10/871,591, Haubrich et al.  
U.S. Appl. No. 10/351,723, Santoso, et al.

*Primary Examiner*—Mark W Bockelman  
*Assistant Examiner*—Roland Dinga

(57) ABSTRACT

A method and system for remotely programming a medical device that includes generating a remote monitoring schedule; establishing a communication link between a centralized programming instrument and an external medical device; and transferring the remote monitoring schedule to the external medical device via the communication link. The remote monitoring schedule is transmitted to an implantable medical device via an established telemetry link between the implantable medical device and the external medical device.

5 Claims, 4 Drawing Sheets

U.S. PATENT DOCUMENTS

| | | |
|---|---|---|
| 2001/0039504 A1 | 11/2001 | Linberg et al. |
| 2001/0051787 A1 | 12/2001 | Haller et al. |
| 2002/0023654 A1* | 2/2002 | Webb ........................ 128/899 |
| 2002/0040234 A1* | 4/2002 | Linberg ...................... 607/32 |
| 2003/0144711 A1 | 7/2003 | Pless et al. |
| 2005/0288736 A1* | 12/2005 | Persen et al. .................. 607/60 |
| 2006/0224186 A1* | 10/2006 | Ziegler et al. ................. 607/2 |
| 2008/0194927 A1* | 8/2008 | KenKnight et al. ......... 600/301 |

\* cited by examiner

REMOTE SCHEDULING FOR MANAGEMENT OF AN IMPLANTABLE MEDICAL DEVICE

RELATED U.S APPLICATION DATA

This is a continuation-in-part of commonly assigned U.S. application Ser. No. 10/871,591, entitled "CONDITIONAL REQUIREMENTS FOR REMOTE MEDICAL DEVICE PROGRAMMING", filed on Jun. 18, 2004, now U.S. Pat. No. 7,565,197 incorporated herein by reference in its entirety.

FIELD OF THE INVENTION

The present invention relates generally to implantable medical device systems and more particularly to methods for remotely programming an implantable medical device (IMD).

BACKGROUND

One goal of a technology-based health care system that fully integrates the technical and social aspects of patient care and therapy is to connect the client with care providers irrespective of separation distance or location of the participants. While clinicians will continue to treat patients in accordance with accepted medical practice, developments in communications technology are making it ever more possible to provide medical services in a time- and place-independent manner.

Past methods of clinical services are generally limited to in-hospital operations. For example, if a physician needs to review the performance parameters of an implantable device in a patient, the patient normally had to go to the clinic. Further, if the medical conditions of a patient with an implantable device warrant continuous monitoring or adjustment of the device, the patient would have to stay in a hospital indefinitely. Such a continued treatment plan poses both economic and social problems. Under this scenario, as the segment of the population with implanted medical devices increases many more hospitals/clinics and service personnel will be needed to provide in-hospital service for the patients, thus escalating the cost of healthcare. Additionally the patients will be unduly restricted and inconvenienced by the need to either stay in the hospital or make very frequent visits to a clinic.

Yet another condition of the past practice requires that a patient visit a clinical center for occasional retrieval of data from the implanted device to assess the operations of the device, gather patient history for both clinical and research purposes and adjust operational settings as needed. Such data is acquired by having the patient in a hospital/clinic to download the stored data from the implantable medical device. Depending on the frequency of data collection, this procedure may pose a serious difficulty and inconvenience for patients who live in rural areas or have limited mobility. Similarly, in the event a need arises to upgrade the software of an implantable medical device, the patient will be required to come into the clinic or hospital to have the upgrade installed.

Thus, there is a need to monitor the performance of the implantable devices on a regular, if not a continuous, basis to ensure optimal patient care. Further, there is a need to program an implantable device in response to such monitoring procedures to optimize the monitoring and therapy delivery functions of the implantable device. In the absence of other alternatives, this imposes a great burden on the patient if a hospital or clinic is the only center where the necessary frequent follow up, evaluation and programming of the medical devices could be made. Moreover, even if feasible, the situation would require the establishment of multiple service areas or clinic centers to provide adequate service to the burgeoning number of patients having implanted devices worldwide. Accordingly, it is vital to have a programmer unit that would connect to an expert medical center to provide access to expert systems and import the expertise to a local environment. This approach would enable unencumbered access to the implanted device or the patient.

To address these needs, a number of proposals have been made to enable remote programming and monitoring of an implantable medical device (IMD) from a centralized patient management system. Using modern communications technologies, data may be transferred from a centralized computer or server to a remote programmer located in the vicinity of a patient for transferring instructions received from the central location to the IMD.

With the inherent advantages of a remote patient management system, potential risks associated with remote IMD programming capabilities include inappropriate programming of an IMD or an adverse response to programming changes occurring when a patient is not under medical supervision. Retrieval of data from the IMD may occur on a scheduled basis, which is generally controlled by timers included in a home monitor or programmer and the IMD. While data may be acquired frequently or even continuously by the IMD, data regarding device performance or physiological conditions may only be transferred to a centralized patient management system during scheduled follow-up interrogation sessions.

BRIEF DESCRIPTION OF THE DRAWINGS

Aspects of the present invention will be readily appreciated as they become better understood by reference to the following detailed description when considered in connection with the accompanying drawings, wherein.

DETAILED DESCRIPTION

The following detailed description provides a practical illustration for implementing various embodiments of the invention and is not intended to limit the scope, applicability, or configuration of the invention in any way. The present invention is directed toward providing a method for adjusting a schedule for retrieving data remotely from an IMD. The term "remote" as used herein with regard to programming and interrogation sessions refers to programming and interrogation operations being performed when the patient having an IMD being programmed or interrogated is not in the direct physical presence of a clinician or user performing the programming or interrogation session.

Figure 1:
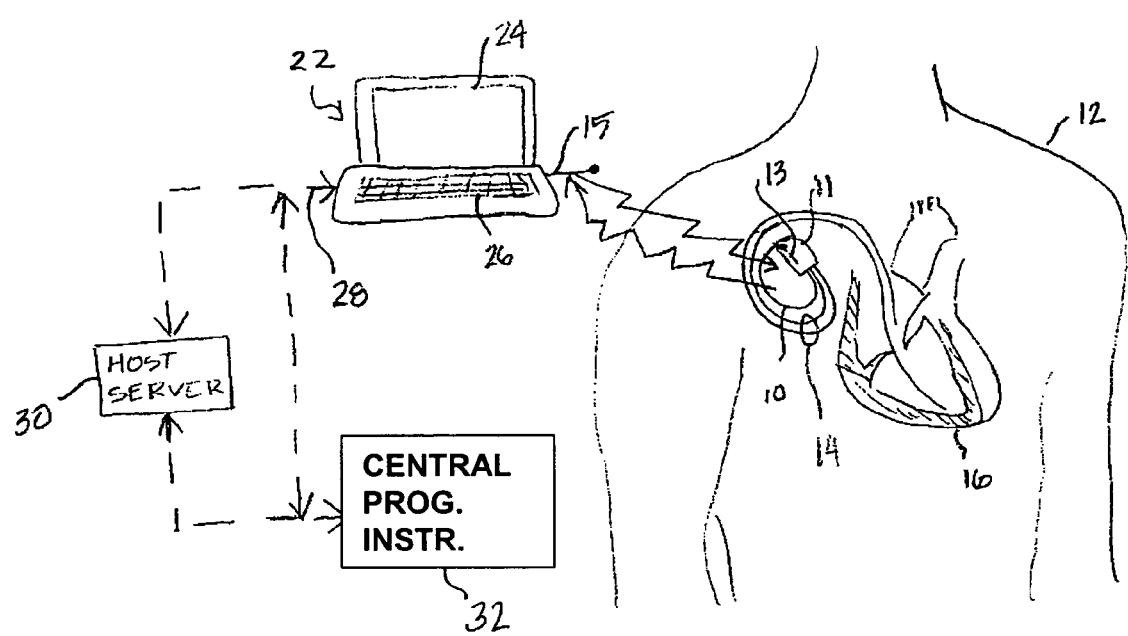
FIG. 1 is a schematic diagram of a medical device system in which embodiments of the present invention may be practiced.

FIG. 1 is a schematic diagram of a medical device system in which embodiments of the present invention may be practiced. A medical device system according to an embodiment of the present invention includes an IMD 10 and an external medical device (EMD) 22. IMD 10 is shown implanted in the body of a patient 12. The present invention may be implemented for use with a variety of programmable IMDs, including cardiac stimulation devices, cardiac or other physiological monitoring devices, neurostimulators, implantable drug pumps, or the like. For the sake of illustration, IMD 10 is shown here as a cardiac stimulation device coupled to a set of leads 14 used for positioning electrodes and optionally other physiological sensors in operative relation to the patient's heart 16. Leads 14 are coupled to IMD 10 via a connector block 11. Examples of cardiac stimulation or monitoring devices with which the present invention may be employed are disclosed in U.S. Pat. No. 5,545,186 (Olson et al.), U.S. Pat. No. 5,987,352 (Klein et al.), and U.S. Pat. No. 6,438,408 (Mulligan et al.).

IMD 10 is adapted for bidirectional telemetric communication with EMD 22 to allow data stored or being acquired by IMD 10 to be retrieved by EMD 22 during an interrogation or monitoring session. EMD 22 is also used to transfer code, operating parameters, or other instructions to IMD 10. EMD 22 is sometimes referred to as a "home monitor" or "home programmer" since it is often located in a patient's home such that it is proximate the IMD 10 to enable communication sessions between EMD 22 and IMD 10. EMD 22 may alternatively be located in a hospital room, clinic or other location. Examples of external devices that may be located in a patient's home or in another remote location capable of telemetric communication with an IMD are disclosed in U.S. Pat. No. 6,647,299 (Bourget), U.S. Pat. No. 6,564,104 (Nelson et al.), U.S. Pat. No. 6,561,975 (Pool et al.), U.S. Pat. No. 6,471,645 (Warkentin et al.) and U.S. Pat. No. 6,249,703 (Stanton et al.), all of which patents are incorporated herein by reference in their entirety. EMD 22 may alternatively be embodied as a mobile device that may be worn or carried by the patient.

Programming commands or data are transmitted between an IMD RF telemetry antenna 13 and an external RF telemetry antenna 15 associated with the EMD 22. The external RF telemetry antenna 15 may be contained in a programmer RF head so that it can be located close to the patient's skin overlying the IMD 10. Such programmer RF heads are well known in the art. See for example U.S. Pat. No. 4,550,370 (Baker), incorporated herein by reference in its entirety. The EMD 22 may be designed to universally program IMDs that employ conventional ferrite core, wire coil, RF telemetry antennas known in the prior art and therefore also have a conventional programmer RF head and associated software for selective use with such IMDs.

Alternatively, the external RF telemetry antenna 15 can be located on the case of the EMD 22, and the EMD 22 can be located some distance away from the patient 12. For example, RF telemetry antenna 15 may be integrated with EMD 22, and EMD 22 may be located a few meters or so away from the patient 12 and utilize long-range telemetry systems. Such long-range telemetry systems allow passive telemetry transmission to occur between IMD 10 and EMD 22 without patient interaction when IMD 10 is within a communication range of EMD 22. Thus, patient 12 may be active, e.g., partaking in normal household activities or exercising during a telemetry transmission. Telemetry systems that do not require the use of a programmer RF head are generally disclosed in U.S. Pat. No. 6,240,317 (Villaseca et al.), U.S. Pat. No. 6,169,925 (Villaseca et al.), and U.S. Pat. No. 6,482,154 (Haubrich et al.), all of which patents are incorporated herein by reference in their entirety.

In an uplink telemetry transmission, the external RF telemetry antenna 15 operates as a telemetry receiver antenna, and the IMD RF telemetry antenna 13 operates as a telemetry transmitter antenna. Conversely, in a downlink telemetry transmission, the external RF telemetry antenna 15 operates as a telemetry transmitter antenna, and the IMD RF telemetry antenna 13 operates as a telemetry receiver antenna. Each RF telemetry antenna is coupled to a transceiver comprising a transmitter and a receiver. Any of a number of suitable programming and telemetry methodologies known in the art may be employed such as the RF encoded telemetry signal system generally disclosed in U.S. Pat. No. 5,312,453 (Wyborny et al.), incorporated herein by reference in its entirety.

EMD 22 is shown in FIG. 1 to be embodied as a home monitor or home programmer used in conjunction with IMD 10. EMD 22 generally includes a display 24, user interface 26, and a control system typically in the form of one or more microprocessors in addition to the telemetry circuitry described above. However, embodiments of the present invention are not limited to being practiced with an IMD system wherein the external device functions as an associated programmer or home monitor. The present invention may alternatively be practiced with an external medical device system wherein a bedside or portable device performs physiological monitoring or therapy delivery functions. For example, EMD 22 may alternatively be embodied as a bedside monitoring console that may include ECG monitoring, blood pressure monitoring, oxygen saturation monitoring, carbon dioxide monitoring, or other physiological signal monitoring.

Whether EMD 22 is associated with an internal or external medical device system, EMD 22 is provided with a communication link 28 that allows EMD 22 to receive information from and transfer information to a remote patient management system including a centralized programming instrument 32. Centralized programming instrument 32 may be located at a clinical center or other patient management facility and be part of an expert system used for remotely managing IMDs. In one embodiment, centralized programming instrument 32 is a dedicated, microprocessor-based device programmed to execute programming operations and coupled to a communication network.

Centralized programming instrument 32 is alternatively implemented as a web-based programming instrument accessible by an Internet-enabled computer system. Centralized programming instrument 32 may alternatively be implemented in programming code on a personal computer. Centralized programming instrument 32 is coupled to a local area network (LAN), wide area network (WAN), telecommunications network, or the like, which allows communication link 28 to be established between central programming instrument 32 and EMD 22. Centralized programming instrument 32 may communicate with EMD 22 via a host server 30, which may be used to control remote programming protocols according to some embodiments of the present invention. Centralized programming instrument 32 may also be accessible from a secondary computer such as a physician's laptop or handheld device via the Internet or other computer network.

It is recognized that a remotely programmable medical device system and associated remote programming methods provided by the present invention may be embodied in a variety of systems, including multiple implantable devices, including various types of EMDs and telemetry systems used for communicating with the IMD(s), and various embodiments of a centralized programming instrument 32 and communication link 28. Centralized programming instrument 32, for example, may be a dedicated instrument or may represent programming functionality implemented in software on an existing computer system or Internet-based web page. Communication link 28 may be established via a modem connection or wireless communication technologies. Additional detailed descriptions of systems for remote management of implantable medical devices in which embodiments of the present invention may be implemented are described in U.S. Pat. No. 6,418,346 (Nelson, et al.), U.S. Pat. No. 6,363,282 (Nichols), U.S. Pat. No. 6,497,655 (Linberg et al.), and U.S. Pat. No. 6,442,433 (Linberg), all of which patents are incorporated herein by reference in their entirety.

Figure 2:
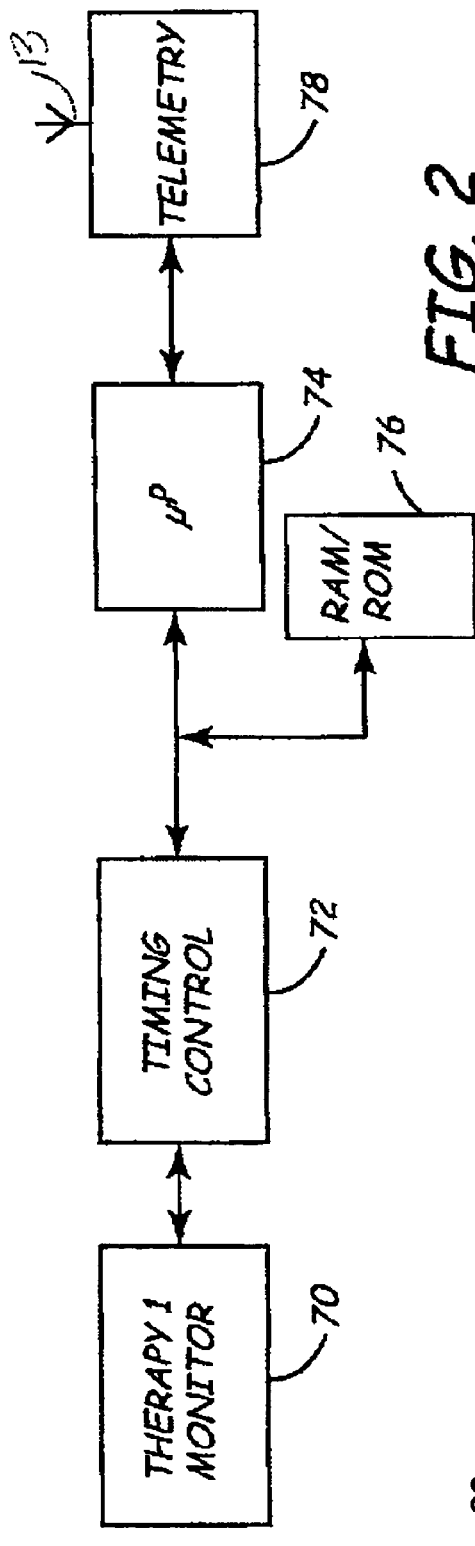
FIG. 2 illustrates typical components of the IMD shown in FIG. 1.

FIG. 2 illustrates typical components of IMD 10 shown in FIG. 1. Major operative structures common to IMD 10 are represented in a generic format. IMD 10 contains timing and control circuitry 72 and an operating system that may employ microprocessor 74 or a digital state machine for timing, sensing and therapy delivery functions in accordance with a programmed operating mode. IMD 10 also contains therapy/monitor 70 which may include sense amplifiers for detecting cardiac signals, patient activity sensors or other physiologic sensors for sensing the need for a therapy, and pulse generating output circuits for delivering cardiac stimulation pulses to at least one heart chamber under control of the operating system in a manner known in the art. The operating system includes memory registers or RAM/ROM 76 for storing a variety of programmed-in operating mode and parameter values that are used by the operating system. The memory registers or RAM/ROM 76 may also be used for storing data compiled from sensed cardiac activity and/or relating to device operating history or sensed physiologic parameters for telemetry out on receipt of a retrieval or interrogation instruction. These functions and operations are known in the art, and generally employed to store operating commands and data for controlling device operation and for later retrieval to diagnose device function or patient condition.

Programming commands or data are transmitted between IMD 10 RF telemetry antenna 13 and an external RF telemetry antenna 15 associated with EMD 22, as described previously. RF telemetry antenna 13 is coupled to a telemetry transceiver 78. The telemetry transceiver 78 is coupled to control circuitry and registers operated under the control of microcomputer 74. The telemetry transceiver 78 is typically in a low-power state until being "woken-up" for a telemetry session. Telemetry transceiver 78 then operates in a high-power state for sending and receiving data.

Telemetry transceiver 78 may be woken up automatically at programmed intervals of time. One or more timers may be set such that upon expiration of a timer telemetry transceiver 78 wakes up and waits for communication from the EMD. A programmed follow-up interrogation schedule may be implemented using timers for causing the IMD telemetry transceiver 78 to automatically wake up at programmed intervals and wait for an interrogation request from the EMD. In some embodiments, telemetry transceiver 78 is manually woken up with the use of a magnet, tapping or other intervention by the patient or another caregiver.

Figure 3:
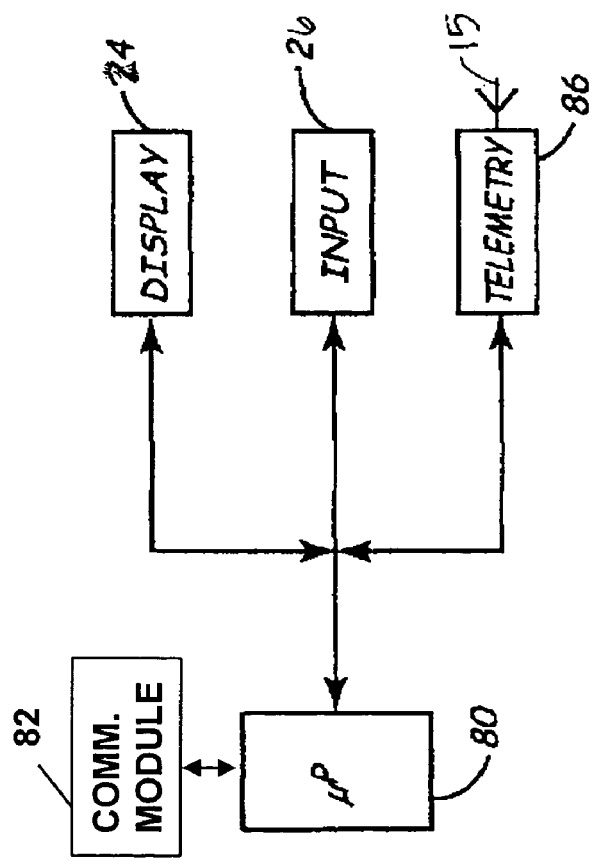
FIG. 3 is a simplified block diagram of major functional components typically included in the external medical device shown in FIG. 1.

FIG. 3 is a simplified block diagram of major functional components typically included in an EMD, such as EMD 22 shown in FIG. 1. The external RF telemetry antenna 15 on EMD 22 is coupled to a telemetry transceiver 86, which includes an antenna driver circuit board having a telemetry transmitter and telemetry receiver. The telemetry transmitter and telemetry receiver are coupled to control circuitry and registers operated under the control of microcomputer 80. Telemetry transceiver 86 is used for telemetric communication with IMD 10. EMD 22 further includes a communication module 82, which may be a hardwired or wireless modem or other communication interface, such as Bluetooth, WiFi, 802.11, or the like, for coupling EMD 22 to a communications network to enable data to be transferred between EMD 22 and the centralized programming instrument or generally to a remote patient management system.

EMD 22 may be a personal computer type, microprocessor-based device incorporating a central processing unit 80, which may be, for example, an Intel Pentium microprocessor or the like. A system bus interconnects CPU 80 with a storage unit such as a disk drive, storing operational programs and data, and with a graphics circuit and an interface controller module. An external storage unit such as a floppy disk drive or a CD ROM drive may also be coupled to the bus and is accessible via a disk insertion slot within the housing of EMD 22. EMD 22 may include solid-state memory for long-term storage of data.

In order for the physician, patient, or other caregiver or authorized operator to interact with the EMD 22, a keyboard or other user interface 26 coupled to CPU 80 is optionally provided. However the primary communications mode may be through graphics display screen of the well-known "touch sensitive" type controlled by a graphics circuit. A user of EMD 22 may interact therewith through the use of a stylus, also coupled to a graphics circuit, which is used to point to various locations on screen or display 24 which display menu choices for selection by the user or an alphanumeric keyboard for entering text or numbers and other symbols. Various touch-screen assemblies are known and commercially available. Display 24 and/or the user interface 26 allow a user to enter command signals to initiate transmissions of downlink or uplink telemetry and to initiate and control telemetry sessions once a telemetry link with an implanted device has been established. Other types of user interaction mechanisms and electronics may be implemented such as voice recognition/response systems.

Display screen 24 is also used to display patient related data, menu choices and data entry fields used in entering the data or messages alerting a patient or user to pertinent programming or monitoring conditions. Display screen 24 also displays a variety of screens of telemetered out data or real time data. Display screen 24 may also display uplinked event signals as they are received and thereby serve as a means for enabling timely review of IMD operating history and status.

EMD 22 may also include an interface module, which includes a digital circuit, non-isolated analog circuit, and/or isolated analog circuit for coupling peripheral or accessory devices or instruments to EMD 22. The digital circuit enables the interface module to communicate with the interface controller module. For example, EMD 22 may be provided with a strip chart printer or the like coupled to interface controller module so that a hard copy of a patient's ECG, EGM, marker channel of graphics displayed on the display screen can be generated. EMD 22 may be of the type generally disclosed in U.S. Pat. No. 5,345,362 (Winkler), which is incorporated by reference herein in its entirety.

Figure 4:
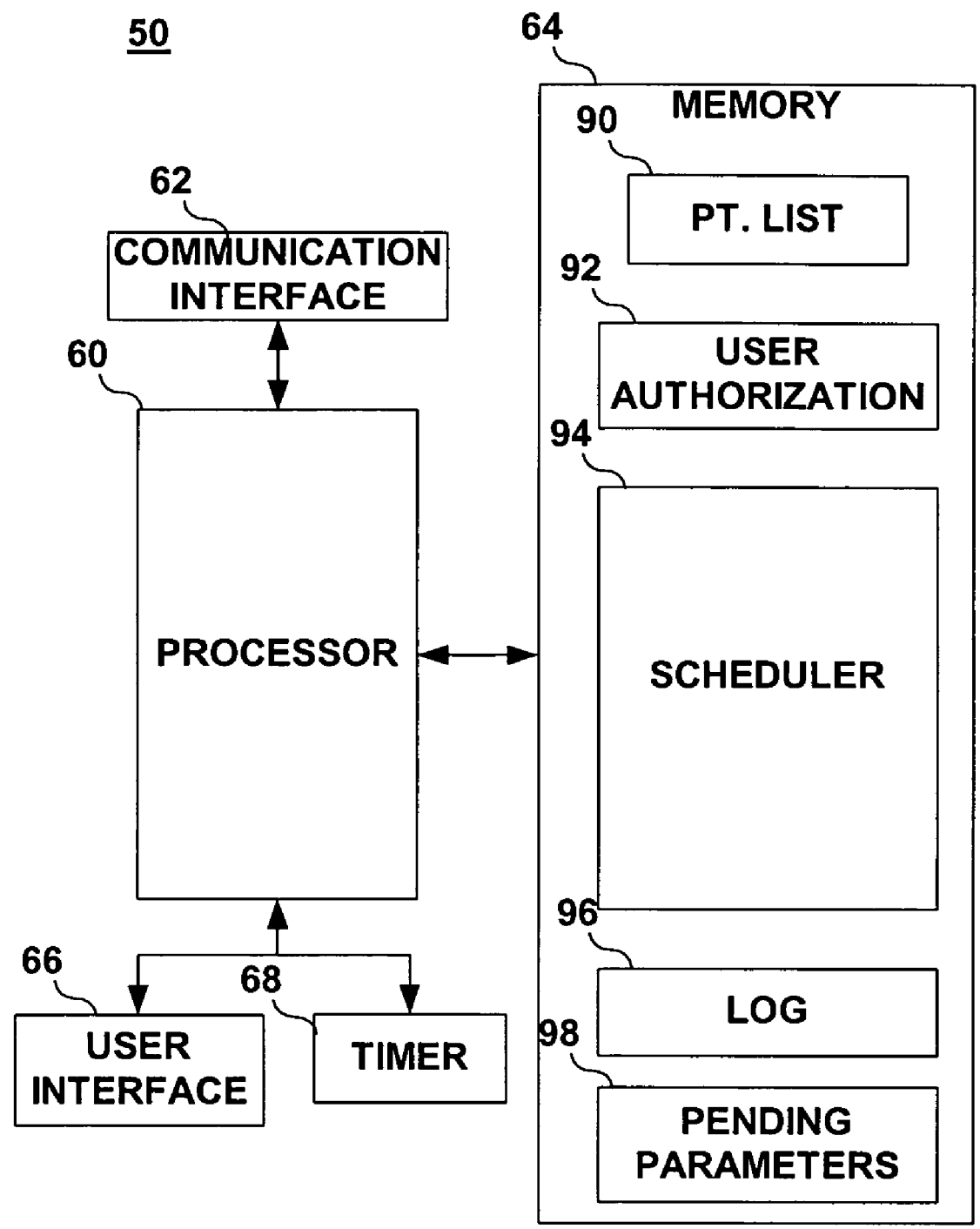
FIG. 4 is a schematic block diagram illustrating functional aspects of a remote patient management system according to one embodiment of the invention.

FIG. 4 is a schematic block diagram illustrating functional aspects of a remote patient management system according to one embodiment of the invention. The centralized programming instrument includes a processor 60 for executing programmable code controlling remote programming operations in conjunction with memory 64. A remote programming session will typically be initiated by a physician, nurse, medical technician or other authorized user, generally referred to hereafter as "user," using the centralized programming instrument. As such a user interface 66 is provided to allow the user to enter log in data, programming data and instructions, and view prompts or other responses provided by the centralized programming instrument.

The processor 60 determines if a user is authorized to perform remote programming of an IMD based on authorization data stored in memory 64. Authorization data queried by processor 60 for verifying that a remote programming session initiated by a user is authorized to proceed includes user authorization 92. A system administrator assigns user log in data and corresponding authorization for performing remote programming, stored in user authorization 92. In particular, a system administrator manages which users are authorized to access a remote scheduler 94 for adjusting the schedule for remote retrieval of IMD data during follow-up interrogation sessions.

Authorization data used by processor 60 for controlling a remote programming session may further include a patient list 90 linked to user authorization 92. The patient list 90 may include patient groupings according to a particular type of IMD, a particular type of diagnosis, having a common primary care physician, a particular risk stratification or other risk-related criteria. A system administrator may determine various patient grouping criteria for which remote programming user authorization status is linked. User authorization data 92 is entered and stored by a system administrator or other authorized personnel to indicate for which patients (or IMDs) a user is authorized to perform remote programming operations. In particular, the patient list 90 and user authorization data 92 are queried by processor 60 to determine if a user is authorized to access scheduler 94 for adjusting the schedule for remotely retrieving data from the targeted patient/IMD.

Scheduler 94 represents code that allows a user to make adjustments to a remote IMD follow-up interrogation schedule. Scheduler 94 may utilize a graphical user interface or web-based screens for presenting a calendar on which a user can select dates and times at which an IMD interrogation session is to occur. A user may enter new interrogation sessions, move previously scheduled interrogation sessions to new times or dates, and/or cancel previously scheduled sessions. Interrogation sessions may be scheduled to occur at a regular frequency according to a designated time interval, such as daily, weekly or monthly. Interrogation sessions may also be scheduled to occur at a variable frequency or irregular intervals. For example, a user may select weekly interrogation session for four weeks and monthly interrogation sessions thereafter. The time of day at which scheduled interrogation sessions occur may be fixed, variable or random. Scheduler 94 may also allow the user to select which data is retrieved, such as monitored physiological data, therapy-related data, or device diagnostic data. Interrogation sessions may be scheduled to retrieve one type of data or a particular parameter according to one data retrieval schedule and another type of data or parameter according to another data retrieval schedule.

Adjustment to a follow-up interrogation schedule may also be programmed to occur automatically in response to data received from the IMD. For example, a user may program a schedule change to occur in response to a programmed level of a monitored physiological parameter or device-related parameter. In one embodiment, a user may program follow-up interrogation sessions to be scheduled at an altered frequency or time in response to data received from the IMD relating to therapy delivery. In another embodiment, a user may program follow-up interrogation sessions to be scheduled to occur at an altered frequency or time in response to a physiological parameter value received from the IMD.

Memory 64 may further include a remote programming log 96 for storing a history of remote programming sessions associated with a given patient or IMD. A user may enter programming notations using user interface 66 for storage in log 96 along with scheduling changes, programmed parameter values, date and time information, patient location information, safety requirements, and other relevant data.

Memory 64 further includes allocated space for storing pending programmed parameter values 98 entered by a user but not yet transferred to a targeted EMD. Pending parameter values may be stored for a defined interval of time controlled by the use of a timer 68. Pending parameter values may be canceled if timer 68 expires prior to establishing communication with an EMD and/or verifying successful transfer of parameter values to a targeted IMD.

The remote programming system 50 includes a communication interface 62 for establishing communication with a targeted EMD for transferring user-entered parameter values and receiving parameter verification and/or programming confirmation transmissions from the EMD. The various functional blocks represented in FIG. 4 may be included in centralized programming instrument 32 or distributed across a remote patient management system. For example, data stored in memory 64 may be included in a computer located in a clinic or on a server and accessed by a computer-implemented or web-based centralized programming instrument.

Figure 5:
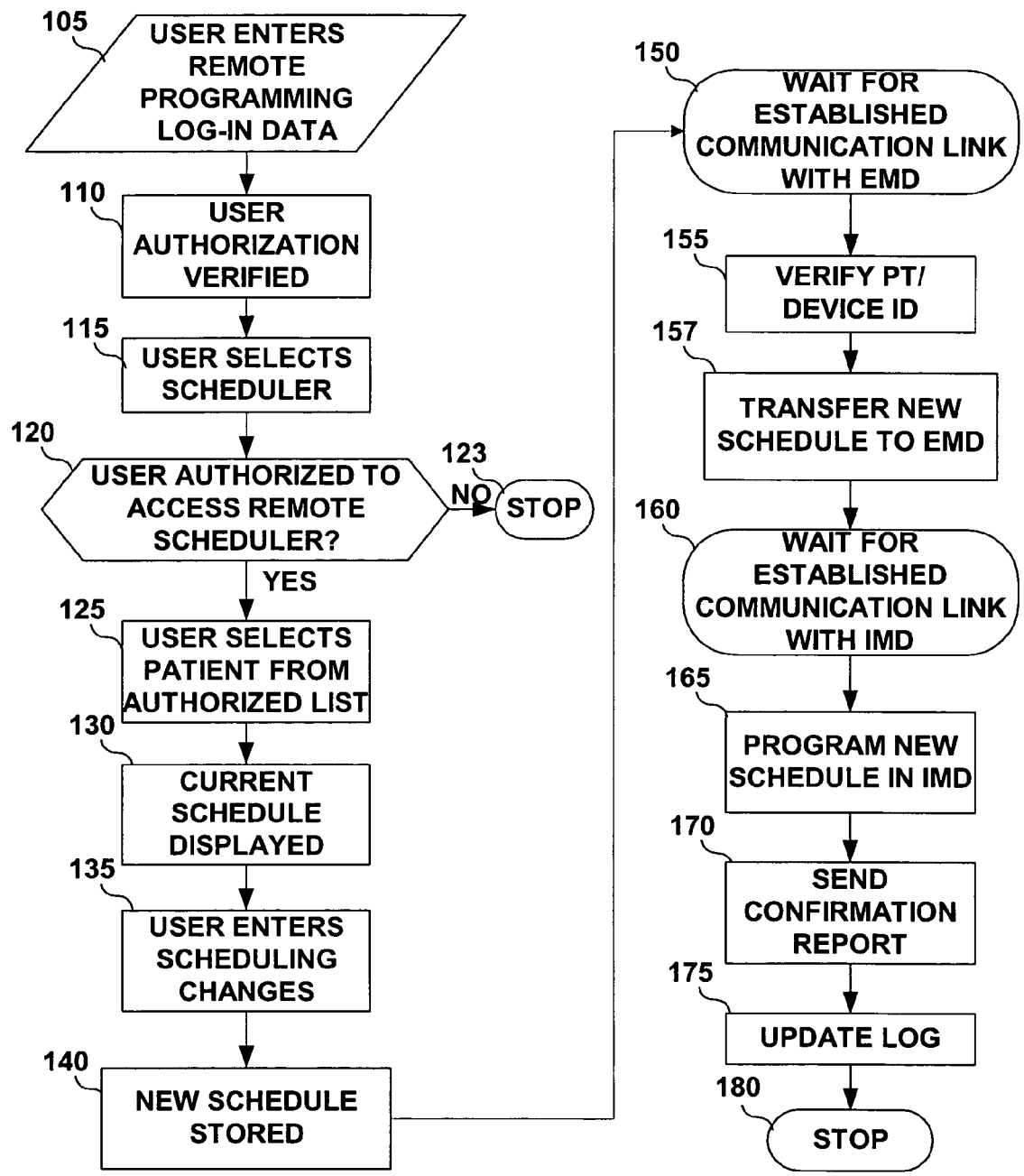
FIG. 5 is a flow chart summarizing steps included in a remote programming method for adjusting an IMD follow-up monitoring schedule according to an embodiment of the invention.

FIG. 5 is a flow chart summarizing steps included in a remote programming method for adjusting an IMD follow-up monitoring schedule according to an embodiment of the invention. A remote programming session is initiated at step 105. The user enters remote programming log-in data using a user interface to gain access to the centralized programming instrument. In one embodiment, the user enters a secure username and password. In other embodiments, the user gains access to the centralized programming instrument via any implemented secure access protocol such as: a public key/private key protocol; biometric authentication methods which may include a retina scan, fingerprint, voice recognition, or facial image; a user-carried token or swipe card; timed random code or key card; or a predetermined specific series of commands. It is appreciated that numerous protocols may be implemented for allowing secure access of authorized users to the centralized programming instrument.

At step 110, the user's identification is verified as an authorized remote programming user according to user authorization data entered by a system administrator. Some users may be allowed to gain access to a remote patient management system to view data, update patient records, or perform other non-programming functions. After verifying the user authorization, the user selects the remote scheduler at step 115. Verification of the user's authorization to make changes to scheduled remote follow-ups is performed at step 120. If the user is not authorized access the remote scheduler, the follow-up scheduling method 100 is terminated at step 123.

If the user is authorized to access the remote scheduler, the user is presented with a patient list at step 125. The user selects a patient for which scheduling adjustments will be performed. The list of patients presented to the user at step 125 includes patients for which the user is authorized to perform scheduling adjustments. The user may select one or more patients from the presented patient list. In some cases, multiple patients may be selected simultaneously for particular scheduling changes, which may apply to numerous patients simultaneously.

At step 130, the current follow-up schedule for the selected patient is displayed to the user. The user enters desired changes to the follow-up schedule at step 135. Changes to the schedule may include the frequency of interrogation sessions, the time of day which interrogation sessions occur, and the data retrieved during a scheduled session.

At step 140, the newly programmed follow-up schedule entered by the user is stored by the centralized programming instrument. Pending programmed values will be stored by the system until a communication link with the appropriate EMD is established. At step 150, the centralized programming instrument waits for a communication link to be established with the appropriate EMD. In some embodiments, the communication link between the centralized programming instrument and the EMD may be available continuously or accessible at any time. In other embodiments, a communication link may be established by the EMD on a scheduled basis to check for pending programmed values. A communication link may also be established when the next scheduled interrogation session occurs with the IMD in accordance with a previously programmed interrogation schedule.

Once a communication link is established, the centralized programming instrument may verify that the EMD is the appropriate EMD associated with the targeted patient and/or IMD identity for the pending schedule changes. Numerous methods for verifying a patient and/or device identification can be used, several of which are described in co-pending U.S. patent application Ser. No. 10/871,591, incorporated herein by reference in its entirety.

After verifying that the EMD with which a communication link has been established is the appropriate one for transferring the pending follow-up schedule, the programming request and scheduling data are transferred to the EMD at step 157. At step 160, the EMD waits for a communication link to be established with the IMD. Generally the IMD "wakes up" the IMD telemetry circuitry according to a previously programmed scheduled basis and establishes a communication link with the EMD. In some embodiments, patient interaction is required to wake-up the IMD telemetry.

The pending programmed schedule is transmitted from the EMD to the IMD at step 165. After successfully transferring the scheduling data, a confirmation report is sent by the EMD to the centralized programming instrument at step 170. Confirmation of successful transmission of the programmed values between the EMD and the IMD can be performed according to telemetry protocols known in the art. Successful transmission may be verified according to protocols for monitoring signal strength, detecting transmission errors, lost data or other subroutines used to verify complete and accurate data transmission. After sending the confirmation report, a remote programming log may be updated at step 175, and the remote programming method is terminated at step 180. The log is updated with the programmed parameters, a notation of the confirmation report receipt and any other relevant information.

Thus, a medical device system and method for performing remote programming of a follow-up interrogation schedule have been presented in the foregoing description with reference to specific embodiments. It is appreciated that various modifications to the referenced embodiments may be made without departing from the scope of the invention as set forth in the following claims.

The invention claimed is:

1. A medical device system, comprising:
    a centralized programming device to generate and store an updated remote monitoring schedule;
    an external medical device comprising a first communication interface communicating with the centralized programming device and a second communication interface, the external device which has received the updated remote monitoring schedule from the centralized programming device along the first communication interface;
    an implantable medical device which has received the updated remote monitoring schedule from the external medical device along the second communication interface and which has adjusted a monitoring schedule of the implantable medical device in response to the received updated remote monitoring schedule, wherein said updated remote monitoring schedule comprises subsequent times said second communication interface will operate in a high power state during communication, and said second communication interface will operate in a low power state following communication and until being woken-up to operate in a high power state.

2. The system of claim 1, further comprising a user interface to input data to the centralized programming device changing the updated remote monitoring schedule generated by the centralized programming device.

3. The system of claim 2, wherein the input data includes one of communication session frequency, communication session time of day, data to be retrieved during a remote follow up communication session, a new communication session to a previous remote follow-up communication schedule, and commands associated with canceling a previously scheduled communication session.

4. The system of claim 2, wherein the communication schedule change corresponds to one of a physiological parameter and a parameter associated with the implantable medical device.

5. A medical device system, comprising:
    a centralized programming device to generate and store an updated remote monitoring schedule;
    an external medical device-comprising a first communication interface communicating with the centralized programming device and a second communication interface, the external device which has received the updated remote monitoring schedule from the centralized programming device along the first communication interface;
    an implantable medical device which has received the updated remote monitoring schedule from the external medical device along the second communication interface and which has adjusted a monitoring schedule of the implantable medical device in response to the received updated remote monitoring schedule, wherein said updated remote monitoring schedule comprises subsequent times said second communication interface will operate in a high power state during communication and after being woken-up.

* * * * *